United States Patent [19]

Haber et al.

[11] Patent Number: 4,803,167

[45] Date of Patent: Feb. 7, 1989

[54] MONOCLONAL ANTIDIGOXTIN ANTIBODIES

[75] Inventors: Edgar Haber, Weston; Meredith Mudgett-Hunter, Hyde Park; Michael Margolies, Weston, all of Mass.

[73] Assignee: The General Hospital Corporation, Boston, Mass.

[21] Appl. No.: 363,545

[22] Filed: Mar. 30, 1982

[51] Int. Cl.⁴ .................. C12N 5/00; G01N 33/53; C07K 15/02

[52] U.S. Cl. .................. 435/240.27; 424/85.8; 530/387; 530/388; 436/548

[58] Field of Search .................. 424/85, 86, 89; 435/172, 240, 241, 948, 240.27; 436/548; 530/387, 388

[56] References Cited

FOREIGN PATENT DOCUMENTS 44441   1/1982   European Pat. Off. ............ 435/240

OTHER PUBLICATIONS

Margolies, M. et al., Monoclonal Antibodies and T Cell Hybrd, pp. 367–374, Elseveer/North Holland Biomedical Press, Amsterdam, 1981.

Zurawski, Jr. et al., J. Immunology, vol. 121, No. 1, 1978.

Mudgett-Hunter et al., Abstracts of Fourth International Congress of Immunology, Paris, No. 19.2.14, 1980.

Novolny et al., FASEB Abstract, 40:1098, 1981.

Bany et al., Scand. J. Clin. Lab. Invest., vol. 41, pp. 75–78 (1981).

Mudgett-Hunter et al., Fed. Proc., vol. 39, No. 3, p. 928 (1980).

Sevier et al., Clin. Chem., vol. 27, No. 11, pp. 1797–1806 (1981).

*Primary Examiner*—Blondel Hazel
*Attorney, Agent, or Firm*—Saidman, Sterne Kessler & Goldstein

[57] ABSTRACT

The present invention discloses a hybridoma culture and high affinity monoclonal antidigoxin antibodies produced by somatic cell fusion. The antibodies are useful for therapeutic as well as for diagnostic purposes. They are also useful in a model system for the study of structure-function relationships in antigen-antibody specific reactions.

2 Claims, 2 Drawing Sheets

MONOCLONAL ANTIDIGOXTIN ANTIBODIES

BACKGROUND OF THE INVENTION

1. Field of the Invention

This invention relates generally to the subject matter of antibodies. More particularly, it relates to monoclonal antibodies to cardiac glycoside, digoxin. The antibodies may also have cross-reactivity with digitoxin.

2. Description of the Prior Art

Digoxin and digitoxin are two of a large group of cardiac glycosides, frequently prescribed for patients with congestive heart failure. Cardiac glycosides are composed of a steroid or aglycone portion and from one to four sugar molecules. The pharmacological activity resides in the aglycone portion of the molecule and the glycoside residues modify water solubility and potency. One of the pharmacodynamic properties of this class of compounds is to increase the force of myocardial contraction.

Digoxin is an uncharged, chemically well defined hapten, sufficient in size to occupy most of the antibody combining site. For this reason, cardiac glycosides which include several structurally related analogs are suitable for the study of antibody fine specificity. But, the rigid four ring structure common among all cardiac glycosides and other steroids does not allow for major conformational changes as functional groups are substituted at various positions on the rigid steroid backbone. However, through an analysis of antibody affinity for related glycosides, it may be possible to determine antigenic determinants specific for a given anti-digoxin antibody. Certain heterogeneous antidigoxin antibodies produced in sheep have been shown to be very specific. They can discriminate between digoxin and digitoxin, which differ by the presence or absence of only a single hydroxyl group on the steroid backbone.

The possibility of reversing digoxin or digitoxin toxicity and correlating variation in the antibody combining site with differences in specificity for closely related haptens prompted the discovery of a source of unlimited supply of monoclonal antidigoxin antibodies. The successful innovation and perfection, for the first time, of the new technique of somatic cell fusion, for the production of an unlimited supply of high-affinity monoclonal antidigoxin antibodies which may also have cross-reactivity with digitoxin now opens the possibility of using such antibodies for the study of antigen-antibody structure-function relationships as well as for diagnostic and therapeutic purposes. Such a technique for the production of antibodies against digoxin has heretofore been unknown in the art.

Among various problems encountered in the somatic cell fusion technology, a major dificulty is the stability of the resulting hybridoma. Prediction, a priori, of hybridoma stability is virtually impossible. Usually after a few months of growth, the hybrids lose their specific function. The reason for this event is not yet known but mutational changes, loss of chromosome or overgrowth because of persistent multiclonality may be some of the factors for the loss of the functional activity of the hybrids. The present invention has overcome such problems and provides a method of producing stable hybridoma capable of secreting monoclonal antidigoxin antibodies. A clone of such a hybridoma, viz., Dig. 35-20, has now been prepared and deposited with the American type Culture Collection, Rockville, Md. and Identified as HB-8113 which culture is incorporated herein by reference.

SUMMARY OF THE INVENTION

It is, therefore, an object of the present invention to provide a technique of somatic cell fusion for the production of stable hybridoma capable of secreting antibodies against digoxin.

It is another object of the present invention to provide a method of producing high affinity monoclonal antidigoxin antibodies.

It is a further object of the present invention to provide a model system for the study and characterization of structure-function relationships between antibody combining sites and specific antigenic determinants.

It is yet another object of the present invention to provide a method for producing an unlimited supply of monoclonal antidigoxin antibodies useful for therapeutic as well as for diagnostic purposes.

Other objects and advantages will become apparent as the description proceeds.

The attainment of these and other objects is made possible by this invention which includes a process for producing monoclonal antidigoxin antibodies comprising:

(a) obtaining a line of somatic cells immunized against digoxin;

(b) combining said somatic cells by fusion with another cell line whereby hybridomas capable of secreting antidigoxin antibodies are produced and (c) isolating said secreted antibodies.

BRIEF DESCRIPTION OF THE DRAWINGS

A more complete appreciation of the invention and many of the attendant advantages thereof will be readily perceived as the same becomes better understood by reference to the following detailed description when considered in connection with the accompanying figures, wherein:

FIG. 1A, Dig 26-10 FIG. 1B, Dig 35-20; and FIG. 1C, Dig 25-54.

DETAILED DESCRIPTION OF THE INVENTION

Figure 1A:
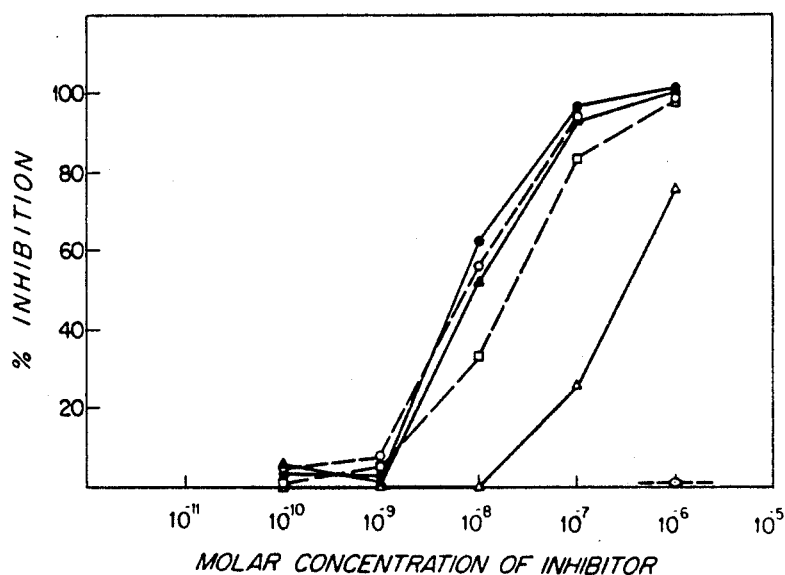
FIG. 1A, FIG. 1B and FIG. 1C are inhibition of binding of various monoclonal antibodies to [$^3$H]digoxin in the dextrancoated charcoal RIA by various cardic glycosides: digoxin (●—●), digitoxin (O----O), digitoxigenin (□—□), acetyl strophanthidin (▲—▲), and ouabain (△—△). No inhibition was found for endogenous steroids: cholesterol, testosterone, 17--estradiol, progesterone, cortisol, and 4-androsterone (-----◇---) in FIG. 1A. Specificity patterns are shown for three monoclonal antidigoxin antibodies.

Basic techniques and facts related to somatic cell fusion and hybridoma technology for the manufacture of monoclonal antibodies has been recently reviewed and described by Jean-Yves Douillard and Thomas Hoffman in Compendium of Immunology, Vol. II, L.

Schwartz, ed., (1981), and is incorporated herein be reference.

Lines of somatic cells immunized against digoxin useful in this invention can be obtained by any suitable immunization technique, including cells which have been sensitized naturally. The host is sensitized by administering the antigen, usually in the form of a protein conjugate, by any suitable method, preferably by injection either intraperitoneally, intravenously, subcutaneously or by intra-foot pad. Adjuvants may be included in the immunization protocol. Virus, bacteria or other cells may also be employed. In vitro sensitization may also be used where only a small amount of the antigen is available or where the immunogen is found to be potentially noxious to the host. Immunized somatic cells are then obtained periodically from the host by the procedures well known to those skilled in the art.

The immunized somatic cells must then be fused with another cell line to produce hybridomas capable of secreting antidigoxin antibodies. Some of the factors to be considered in the selection of another cell line for fusion are rapid, uniform growth characteristics, metabolic deficiency for growth in a specified component of the growth medium and potential for good fusion frequency. Malignant cells have been found to be particularly suitable for fusion. The species from which such cell lines are derived is also an important factor. Intraspecies hybrids, particularly between similar strains, work better than interspecies fusion. Several cell lines including mouse, rat, hamster and human myeloma lines are available and are preferred for obtaining hybridomas.

A variety of fusing agents may be employed to induce cell fusion. Polyethylene glycol and virus induced fusions are particularly efficacious and are the preferred agents.

Rapid identification of suitable hybrids is a key procedure in all hybridoma work. Early detection of hybridoma antibodies may be performed by any suitable assays; particularly preferred are radioimmunoassay, enzyme-linked immunoassay microcytotoxicity assay and the like.

Maintenance of the hybridoma is accomplished by the use of appropriate selection growth medium. Standard tissue culture medium together with feeder cells are usually preferred. Good results are also obtained with Iscove's or Dulbecco's modified Eagle's medium. Hybrids may also be grown in horse or calf serum or in serum-free media and the like.

Hybrids obtained by fusion are heterogeneous colonies. In order to get a homogeneous line expressing a given function, these colonies are preferably cloned. By cloning is meant the process of achieving growth of a cell line from a single parental cell, viz., a monoclonal expansion. Such cloning may be achieved by any suitable technique, preferably by limiting dilution technique, by agarose technique or the like.

Antibody secreting hybrids grown in tissue culture flasks yield supernatant with variable concentrations of antibody, usually in the range of about 10–100 $\mu$g/ml. Higher yields are, therefore, obtained preferably by transferring hybrids into animals with inflammatory ascites. Ascites are preferably induced by intraperitoneal injection of the hybridoma or by other suitable methods.

Preservation of the hybridoma is important and may be accomplished by any suitable technique. A preferred method is by subcloning or by freezing adequate amounts of the hybridoma early after fusion and to reclone the cell population as needed.

The term "hybridoma" as used herein refers to hybrid cells obtained by the technique of somatic cell fusion as described in this specification, the hybrid cells so obtained having the capability of producing antidigoxin antibodies.

The term "monoclonal antibodies" as used herein refers to antibodies produced by a homogeneous line of a cloned colony of cells derived from a single parental hybridoma.

The invention hereof is now further illustrated by the description of the preferred embodiments detailed below.

DESCRIPTION OF PREFERRED EMBODIMENTS

Preparation of Hapten Protein Conjugates

Digoxin (Sigma Chemical Co., St. Louis, Mo.) was covalently coupled through its terminal digitoxose moiety to a number of proteins as described by Smith et al in *Antibodies in Human Diagnosis & Therapy*, eds. E. Haber and R. Krause, Raven Press, N.Y. 1977 and incorporated herein by reference. Digoxin was coupled to human serum albumin (Miles Laboratories, Inc., Elkhart, Id.) (DigHSA); bovine serum albumin (Dig-BSA), and hymocyanin (Worthington Biochemicals) (Dig-Hy). Dig-HSA was used as immunogen; Dig-BSA coupled to cyanogen bromide activated Sepharose as described by Cuatrecasas et al, Biochem. 11:2291 (1972) was used as immunoadsorbant (see below); and Dig-Hy was used as antigen in the polyvinyl chloride (PVC) plate RIA (See below). The crossreactive cardiac glycoside ouabain was similarly coupled to diaminodiproylamine by a periodate oxidation method described by Zurawski et al, J. Immunol. 121:122 (1978), to cyanogen bromide activated Sepharose 4B according to Cuatrecasas et al (1972), supra. This ouabain-amine sepharose immunoadsorbant was employed in the purification of anti-digoxin antibody from ascites (see below).

Selection of Mouse Strain for Immunization

The primary in nitro response to the hapten digoxin (Dig-HSA) was investigated in four strains of mice Balb/c, SWR/J, RF/J and A/J, by the splenic foci technique described by Sigal et al, J. Immunol, 68:1354 (1975) incorporated herein by reference. Surprisingly, only A/J mice gave a significant positive primary response to digoxin. The frequency of digoxin specific precursor B cells in adult A/J mice was determined to be 1/35,000 which agreed well with restricted frequencies determined in Balb/c mice for other haptens such as phosphorylcholine (1/50,000), and p-azophenyl arsonate (1/65,000) reported by Sigal et al (1975), supra, and Sigal, J. Immunol. 119: 1129 (1977), respectively. A/J mice thus discovered to be most responsive, were selected as the strain of choice in subsequent fusion experiments.

Immunizations

For the purpose of fusion, A/J mice were immunized intraperitoneally four weeks prior to fusion with 0.2 ml of an emulsion composed of a 1:1 mixture of complete Freunds' adjuvant (CFA) and 0.1 mg Dig-HSA. Three days prior to fusion, mice were boosted intravenously with 0.01 mg Dig-HSA in saline.

A pool of mouse antidigoxin antibody was prepared from immune sera as follows. A/J mice immunized with Dig-HSA as described above, were bled from the tail on the 3rd or 4th week following intraperitoneal injection of antigen. Their sera were pooled and the antidigoxin antibodies were purified from the sera by affinity chromatography as described below. This antibody preparation was used as a standard antidigoxin reagent in the PVC-plate RIA (described below).

Antisera specific for digoxin was prepared in sheep as previously described by Curd et al, Proc. Nat. Acad. Sci. 65: 2401 (1971). High affinity antidigoxin sheep antisera was used in the clinical RIA for digoxin (described below).

In order to prepare antibody specific for mouse Fab used in the PVC-plate RIA, a goat (*Capra hircus*) was immunized with Fab fragments prepared from normal mouse IgG (see below). The goat was immunized with 5 mg of mouse Fab fragments in CFA at intervals of one month and bled monthly two to three weeks following each immunization.

Cell Lines and Media

Fusions were initially carried out with myeloma cell lines 45.6TG1.7 (Margolies, Cell 8:405 (1976)) which secretes Ig2b,k myeloma protein and P3-NS1/1-Ag4-1 (NSI), [kappa](Kohler et al, Eur. J. Immunol. 6:292 (1976). It was discovered that the presence of myeloma proteins and kappa were problematic because they produced mixed chain molecules. This problem was overcome by the use of nonsecreting cell line. Therefore, later the nonsecreting line SP2/O-Ag14 (SP2/0) (Shulman et al, Nature, 276:269 (1978)) was used exclusively in order to avoid the problem of mixed chain molecules for affinity and structure studies. All cell lines, including hybridomas, were maintained in Dulbecco's modified Eagle medium (DMEM) (Microbiologic Associates, Inc., Walkersville, Md.) supplemented with 20% fetal calf serum (FCS) (Flow Laboratories, McLean, Va.), 50 [m]g/ml gentamycin and 580 [m]g/ml glutamine. Hybrids were selected in HAT medium and subcloned in HT medium (HAT minus aminopterin) as described by Littlefield, Science 145:709 (1964) and incorporated herein be reference.

Somatic Cell Fusion

Fusion was performed by a modification of the procedure described by Marshak-Rothstein et al, J. Immunol. 122:2491 (1979), incorporated herein by reference. Spleen cell suspensions were depleted of red blood cells by ammonium chloride lysis (Boyle, w., Transplant. Genet. 6:761 (1968)). All centrifugations were done at $700 \times g$ for 5 minutes at room temperature unless otherwise noted. Approximately $10^8$ immune spleen cells were mixed with $10^7$ mouse myeloma cells, centrifuged, resuspended in 20 ml of serum-free DMEM medium and centrifuged again. After discarding the wash media, the tube was tapped sharply to disperse the cell pellet. The cells were suspended in 1 ml of 30% (V/V) of polyethylene glycol-1000 (PEG) (Sigma, St. Louis, MO) in serum-free DMEM for 6 minutes. During the 6 minute period the cell suspension was centrifuged at $150 \times g$ for 3 minutes. Thereafter, 20% FCS-DMEM medium was added to the tube and the cell pellet resuspended by tapping the tube. The cells were cultured for 48 hours in $100 \times 17$ mm petri dishes in a humidfed incubator at 37° C. in an atmosphere of 7% $CO_2$. After two days, the cells were transferred to a 50 ml conical tube (Falcon), centrifuged and resuspended in HAT medium. Aliquots (0.1 ml) were distributed into flat bottom 96-well microtiter dishes (COSTAR) at approximately $10^6$ cells per well. During the next two weeks fresh HAT medium was added to the cells every three days. the wells were screened visually for cell growth and the culture media screened for antidigoxin antibody by a radioimmunoassay (described below).

Solid Phase Radioimmunoassay for Antidigoxin Antibody

The radioimmunoassay used for screening culture media from fusion wells for antidigoxin antibody is based on that reported by Klinman et al, Ann. Immunol. (Paris), 127C 489 (1976), incorporated herein be reference. Briefly, wells of polyvinyl chloride microtiter plates are coated with 25 µl of a solution of Dig.-Hy in borate buffered saline overnight at 4° C. After 18 hrs at 4° C., unadsorbed Dig-Hy solution was removed from the wells and the plates were extensively washed with distilled water. Two hundred µl of 10% horse serum in PBS was added to each well and incubated at room temperature for two hours. The plates were again washed extensively. Then 26 µl of culture medium or standard antidigoxin antibody solution was added and incubated for 3–4 hours at room temperature. After washing, the plates were incubated overnight at 4° C. with 50 µl of radioiodinated affinity purified goat antimouse Fab $I^{125}$-G[alpha]MFab. After rinsing, wells were dried and cut from the PVC microtiter plates using a hot wire and counted in a gamma counter.

Radioiodination was carried out by the chloramine T method (Greenwood et al, Biochem., J. 89:114 (1963)) at a ratio of 1 mCi of $I^{125}$ to 30 µg of purified antibody. About 25,000 cpm of the reagent was added in 50 µl to each well in the RIA. The sensitivity of this radioimmunoassay as developed for antidigoxin binding is 0.2 ng antibody.

In order to determine the heavy chain isotype of the antibody bound to Dig-Hy antigen coating the PVC plates, goat antimouse isotypic reagents (Maloy, Springfield, VA) were affinity purified, radioiodinated, and used in place of $I^{125}$-G[alpha]MFab in the radioimmunoassay described above. Typically, goat or rabbit antimouse IgG1, antiIgG2a, anti-IgG2b, anti-IgG3 anti-IgM, and anti-IgA were purified on affinity columns composed of Sepharose 4B coupled to the mouse myelomas with the appropriate isotypes purchased from Litton Bionetics (Kensington, MD) (IgG1 (MOPC 21), IgG2a(UPC10), IgG2b(MOPC 195), IgG3-(MOPC104E), IgA(EPC 109).

Subcloning Mixed Hybridomas

Hybridoma cell populations identified by RIA as secreting antidigoxin antibody were subcloned by limiting dilution on feeder layers of either murine 3T3 cells or nonimmune mouse spleen cells ($10^5$ per microtiter well). Monoclonal antidigoxin antibody secreting cell lines were again identified by the PVC plate radioimmunoassay described above. One hybridoma, Dig 35-20, was subcloned on soft agar as described by Marshal-Rothstein et al (1979), supra. This same line was subcloned for a second time by limiting dilution.

Amplification in the Ascites Form

Each cloned hybridoma cell line was grown in tissue culture and amplified in the ascites form in eight week old CAF/J (F) (Balb/c x A/J) mice. Cells $(0.5-1.0\times10^6)$ are injected intraperitoneally into mice which had been primed two weeks previously with pristane (0.5 ml) (Pfaltz and Bauer, Inc., Stamford, Conn.). Within 10–21 days of injection, ascites containing secreted antidigoxin hybridoma proteins was tapped repeatedly. Ascites collected from individual mice were pooled, centrifuged (1200 rpm) to remove cells, and stored at −20° C. until used. A few drops of 10% azide solution was added to each ascites pool prior to freezing.

Purification of Hybridoma Proteins

Digoxin specific hybridoma proteins were purified from ascites by a variety of chromatographic methods including ion exchange chromatography on DEAE cellulose in 0.02M $KPO_4$ pH 8.0, and affinity chromatography on Dig-BSA-Sepharose or ouabain-amine-Sepharose (as referred to hereinabove). Elution of antibody from either affinity column was accomplished with 3M $NH_4SCN$, 5% acetic acid or 5M guanidine HCl. The $NH_4SCN$ eluted fractions were extensively dialyzed against PBSA. Purity of the resulting antibody fraction was assessed by SDS gel electrophoresis (Steiner et al, Biochemistry, 10:4725 (1971)), cellulose acetate electrophoresis (Chen et al, Proc. Natl. Acad. Sci. USA, 71:1995 (1974)) and N-terminal amino acid sequence determination.

Affinity Determination of Antidigoxin Hybridomas

Average intrinsic association constants $K_o$ were determined for each subcloned antidigoxin hybridoma present in the culture media and following purification from ascites. A radioimmunoassy utilizing $H^3$-digoxin (New England Nuclear, Boston, Mass.) and dextran coated charcoal to separate free $H^3$-digoxin from antibody-bound digoxin was used. This method has been shown previously to yield affinity data comparable to those obtained by equilibrium dialysis using rabbit anti-ouabain antisera (Smith, J. Clin. Invest. 51:1583 (1972)). Briefly, constant amounts of anti-digoxin antibody are added to tubes containing varying amounts of $H^3$-digoxin ($10^8$ to $10^{10}$g) in 1 ml 10% horse serum in PBS. After one hour incubation at room temperature, Dextran coated charcoal was added with mixing to selectively adsorb any free $H^3$-digoxin. After 5 minutes the sample was centrifuged at $8000\times g$ for 15 minutes to pellet the charcoal. Supernatant containing antibody-bound $H^3$-digoxin was decanted and counted in liquid scintillation media. The affinity constant $K_o$ was determined from the Sips equation as modified by Nisonoff and Pressman, J. Immunol. 80:417 (1958):

$$1/b = 1/K_o(Ab)\times 1/c + 1/(Ab)$$

where b is the molar concentration of bound digoxin, c is the molar concentration of free digoxin, and (Ab) is the concentration of antigen binding sites. In contrast to heterogeneous antisera, a linear plot of 1/b versus 1/c is expected for monoclonal hybridoma antibodies.

Specificity Determination

The specificity of each antidigoxin antibody for related cardiac glycosides was assessed by the inhibition of binding of antibody in the dextran charcoal radioimmunoassay Smith (1972), supra. To a constant amount of $H^3$-digoxin (1.5 ng) in 1 ml of buffer is added different amounts ($10^4$ to $10^9$ M) of various cardiac glycosides: digoxin, digitoxin, digitoxigenin, digoxigenin, acetylstrophanthidin, ouabain, deslanoside, and endogenous steroids such as chloresterol, cortisol, androsterone, 17-[beta]-estradiol, progesterone, and testosterone. After 5 minutes, a constant amount of anti-digoxin antibody was added and the assay was continued as described above. Comparison among different antidigoxin antibodies with respect to their fine specificity was made by determining the amount of cardiac glycoside required to achieve 50% inhibition relative to that required for cold digoxin.

Clinical RIA for Digoxin

The dextran coated charcoal RIA described above was also used to quantitate the amount of digoxin in sera from patients at the Massachusetts General Hospital (smith et al, N. Engl. J. Med. 281:1212-16 (1969)). Amounts of digoxin (ng Digoxin/ml) in sera were determined by a comparison with a standard digoxin inhibition curve generated for each antibody tested (i.e., sheep antidigoxin sera, hybridomas Dig 26-10 and Dig 35-20).

Isoelectric Focusing

Analytical isoelectric focusing (IEF) in polyacrylamide gel (pH 5 to 10) was carried out on an LKB Multiphor apparatus as described in LKB application note 200. The gels were fixed in 10% TCA (4 hours), washed, stained for 12 hours with 0.01% Coomassie Brilliant Blue in methanol:water:acetic acid (5.0:4.5:0.5, V/V) and destained in water:methanol:acetic acid (7.25:2.0:0.75, V/V).

Preparation of Fab

Fab fragments were prepared from purified antidigoxin protein or normal mouse IgG by papain digestion (Porter, Biochem. J. 73:119 (1959)), and purified by ion exchange chromatography on DEAE cellulose equilibrated with 0.005M $KPO_4$ buffered at pH 8.0. Normal mouse Fab was coupled to cyanogen bromide activated Sepharose (Cuatrecasas (1972) supra, and used for affinity purification of GaMFab.

Production of Monoclonal Anti-Digoxin Antibodies

Spleen cells from A/J mice immunized with Dig-HSA were fused with one of the following myeloma cell lines: 45.6TG1.7, NS-1, or Sp2/0. As shown in Table I, the number of wells exhibiting cell growth and the number secreting antidigoxin antibody varied with the myeloma cell line used.

TABLE I

Fusion Summaries for Hybridoma Cell Lines Secreting Anti-digoxin Anitbody

| Fusion Number | Fusion Cell Line | Cultures Positive for Cell Growth (No.) | Fusion Frequency % | Cultures Positive for Anti-Dig Ab (No.) | Established Hybridomas |
|---|---|---|---|---|---|
| 24 | 45.6 TG 1.71 | 292 | 76 | 70 | 1 |
| 25 | NS-1 | 384 | 100 | 162 | 5 |
| 26 | SP2/0 | 38 | 10 | 5 | 5 |

TABLE I-continued
Fusion Summaries for Hybridoma Cell Lines Secreting Anti-digoxin Anitbody

| Fusion Number | Fusion Cell Line | Cultures Positive for Cell Growth (No.) | Fusion Frequency % | Cultures Positive for Anti-Dig Ab (No.) | Established Hybridomas |
|---|---|---|---|---|---|
| 35 | SP2/0 | 7 | 2 | 5 | 1 |

Typically the fusion frequency varied form 76%–100% for the 45.6TG1.7 and the NS-1 lines, and to 2%–12% for the SP2/0 line. The cell lines which fused with the highest frequency also produced the higher yield of hybridomas secreting antibody specific for digoxin: 70 for 45.6TG1.7 and 162 for NS-1. Cells from microtiter culture wells with reactivity to digoxin were subcloned by limiting dilution or on soft agar. It should be noted that more than one half of the selected hybrids lost their their ability to secrete antibody during the cloning procedure. Subcloned hybridoma cell lines actively secreting anti-digoxin antibody were expanded in culture and injected into pristane primed CAF/J (F1 (Balb/c ×A/J)) mice. Ascitic fluid was removed by paracentesis, pooled, and used as a source of antibody. An average range of 5–15 ml of ascites was obtained from individual mice. Frequently hybridoma cell lines actively secreting antibody in culture failed to produce significant antibody titers in ascites. For example, ascites from three of five established cell lines from an NS-1 fushion showed greatly diminished titers in the PVC-RIA. One line from an Sp2/0 fusion (Dig 26-10), when continued in culture, exhibited diminished antibody secretion. Stable antibody production, however, can be regained when subcloned a second time. Such cell lines have now been successfully maintained for a period of two years. During this time, aliquots of Dig. 26-10 cells have been repeatedly thawed, grown in culture and injected in pristane primed mice for ascites production with no loss of antibody activity.

Determination of Monoclonal Antibody H-Chain Isotype

Fusion products secreting antidigoxin antibody were detected by a solid-phase RIA which utilizes affinityrified $I^{125}$-G αM Fab as described supra. Since this probe detects all immunoglobulin isotypes, H-chain isotype was determined separately. All of the four monoclonal cell lines produced from fushion 26 were identified as IgG2a. Like the parent myeloma MOPC 11, Dig 24-2F8 was found to be IgG2b. H-chains of hybridomas Dig 25-54 and Dig 35-20 were both IgG1.

Purification of Antibody from Ascites

Monoclonal anti-digoxin antibodies were purified from ascites either by ion exchange chromatography or by affinity chromatography on Dig-BSA-Sepharose or on ouabain-amine-Sepharose (Table II).

TABLE II
Purification of Monoclonal Anti-digoxin Antibody from Ascites

| Hybridoma | Chromatography | Eluant | Yield (mg Ab/ml ascites) |
|---|---|---|---|
| Dig 24-2F8 | Dig-BSA-Sepharose | 3 M NH4SCN | 0.4 |
|  | Ouabain-Sepharose | 2 M NH4SCN | 1.8 |
| Dig 25-54 | Dig-BSA-Sepharose | 3 M NH4SCN | 3.7 |
|  | DEAE-cellulose | 0.02 M KPO4 | 3.5 |
| Dig 26-10 | Dig-BSA-Sepharose | 3 M NH4SCN | 1.3 |
|  | Ouabain-Sepharose | 3 M NH4SCN | 2.9 |
|  |  | 5% HOAc | 1.4–3.7 |
|  |  | 5% HOAc, 5 M GuHCl | 2.9 |
|  |  | 3 M KSCN, 5 M GuHCl | 2.4 |
|  | DEAE-cellulose | 0.02 M KPO4 | 2.3–2.9 |
| Dig 26-20 | Ouabain-Sepharose | 5% HOAc | 3.1 |
| Dig 26-30 | Ouabain-Sepharose | 5% HOAc | 1.3 |
| Dig 26-40 | Ouabain-Sepharose | 5% HOAc | 1.9 |
| Dig 35-20 | Dig-BSA-Sepharose | 5% HOAc | 0.9 |
|  | Ouabain Sepharose | 3 M NH4SCN, 5% HOAc | 1.3 |

Dig 25-2F8, 25-54, 26-10, and 35-20 adsorbed to the DigBSA column were eluted with NH4SCN or 5% acetic acid. Following extensive dialysis against PBSA, reactivity to digoxin was regained in the eluted fraction in all cases, as assessed by two different RIAs described herein supra. As seen in Table II, however, antibody yields from the Dig-BSA affinity column, were low (0.4 to 1.3 mg/ml ascites) when compared to the other methods. Affinity purification on ouabain-amine-Sepharose was obtained for hybridomas 26-10, 26-20, 26-30, and 26-40 in higher yields (1.4 to 3.7 mg/ml ascites). Bound antibody was eluted either with 5% acetic acid or 3M NH4SCN, pH 7 or in 5M guanidine hydrochloride (Table II). Following elution with NH4SCN, antibody activity was regained after extensive dialysis against PBSA. Antibody 26-10, eluted from the ouabain affinity column with acetic acid and guanidine:HCL, was dialysed sequentially into 0.01 M Na acetate, 0.15 M NaCl, pH 4.6, and PBSA, pH 7.4. Although 26-10 obtained by this procedure was homogeneous by the criteria of sequence determination (Novotny et al, Fed. Proc. 40:1098 (1981)), these preparations of Dig 26-10 were not suitable for binding studies because they precipitated out of solution on standing in PBSA buffer.

Since very little Dig 25-54 satisfactorily bound ouabain-amine-Sepharose (less than 10%), Dig 25-54 was purified in good yield (3.5 mg/ml ascites) by DEAE chromatography. From 2.3 to 2.9 mg/ml antibody 26-10 per ml ascites was obtained when this antibody was similarly purified by DEAE chromatography.

It should be noted that the yields of antibody reported in Table II are given as mg antibody per ml of ascites applied to the column. In most cases, the capacity of the affinity columns to remove antibody was not exceeded as judged by removal of the dominant immunoglobulin band when the fall-through fraction was subjected to zonal electrophoresis. Since no attempt was made to determine the concentration of anti-digoxin antibody in each pool of ascites prior to purification, the yields obtained may also reflect variations in antibody concentrations in different pool of ascites. In general, the concentration of monoclonal antibody present in ascites fluid ranged from 1 to 5 mg/ml, depending on the particular monoclonal cell line and on the time following injection of cells. Ascites tapped from mice earlier than 10 days after injection of the cell line have a lower concentration of monoclonal antibody (less than 1 mg/ml) than ascites taken from mice at 12 to 20 days post-injection (2–5 mg/ml). Purity of antibody preparations obtained by the methods described above was assessed by at least one of the following criteria: single band on zonal electrophoresis, single heavy and light chain bands on SDS electrophoresis, restricted banding pattern on IEF and a single amino acid sequence on N-terminal sequence determination of heavy and/or light chains (40 cycles) (Novotny et al, Fed. Proc. 40:1098 (1981)).

Affinity Determination for Monoclonal Antibodies

Using the dextran coated charcoal binding method for separation of bound antibody from free $H^3$-digoxin (Smith, J. Clin. Invest. 51:1583 (1972)), affinities ($K_o$) for monoclonal anti-digoxin antibodies were determined for antibody present in culture media and in preparations purified from ascites. Data were plotted according to a modified Sips equation (Nisonoff et al, J. Immunol. 80:417 (1958)), as described earlier herein. Typical of single component systems, a linear plot was obtained for all hybridomas analyzed. Correlation coefficients (r) varied from 0.989 to 0.999 for the monoclonal antibodies analyzed by this method. As anticipated, no significant difference was found for affinity constants determined for antibody present in culture media and in preparations following purification from ascites fluid (Table III).

TABLE III

Antibody Affinity Constant for Digoxin

| Anti-digoxin Antibody | H-Chain Isotype | Affinity Constant $K_0(M^{-1})^a$ Culture Media | Antibody Source Ascites[b] or Serum |
|---|---|---|---|
| Monoclonal Antibody: | | | |
| Dig 26-10 | λ2a | $8.5 \times 10^9$ | $4.7 \times 10^9$ |
| | Fab | — | $1.2 \times 10^9$ |
| Dig 26-20 | λ2a | $1.4 \times 10^9$ | $3.4 \times 10^9$ |
| Dig 26-30 | λ2a | $3.9 \times 10^9$ | $5.8 \times 10^9$ |
| Dig 26-40 | λ2a | $4.4 \times 10^9$ | $2.6 \times 10^9$ |
| Dig 25-54 | λ1 | $2.6 \times 10^8$ | $5.2 \times 10^8$ |
| Dig 35-20 | λ1 | $1.9 \times 10^9$ | $1.3 \times 10^9$ |
| Heterogeneous Antibody: | | | |
| Sheep Antisera | — | — | $1.2 \times 10^{10}$ |
| Pooled mouse[c] antisera | — | — | $3.1 \times 10^9$ |
| Pooled mouse antibody | — | — | $3.5 \times 10^9$ |

[a]Affinity constants ($K_0$) were determined in an RIA which utilizes [$^3$H]digoxin and dextran-coated charcoal to adsorb free [$^3$H]digoxin. Data were plotted according to a modified Sips equation. Correlation coefficients varied from r = 0.989–0.999.
[b]Monoclonal antibody was purified from ascites prior to affinity measurements.
[c]Sera from several A/J mice were pooled and the antidigoxin antibodies were purified by affinity chromatography.

The affinity constant determined for Dig 26-10 (approximately $10^9 M^{-1}$) was confirmed by equilibrium dialysis. In addition to sharing H-chain isotype (IgG2s), Dig 26-10 and its sister hybridomas, Dig 26-20, 26-30, and 26-40 have very similar affinity constants in the range of 1.4 to 8.5 x $10^9 M^{-1}$. The $K_o$ determined for Dig 35-20 was also high, $1.3$–$3.4 \times 10^9 M^{-1}$. In contrast to the other hybridomas, $K_o$ for Dig 25-54 was found to be an order of magnitude less, i.e., 3.5 to 5.2 $\times 10^8 M^{-1}$. It is clear from these results that the functional parameters and efficacy of a hybridoma cannot be predicted and must be determined experimentally.

The Fab fragment was prepared from Dig 26-10 and its affinity determined as for the whole antibody. As seen in Table II, the affinity of the Dig 26-10 Fab remained high ($1 \times 10^9 M^{-1}$), only slightly decreased from the average value obtained for the intact antibody ($K_o < 5 \times 10^9$).

Antibody Specificity Determination

Specificity of monoclonal antibody binding site for related cardiac glycosides was examined by means of hapten inhibition experiments in which the binding of monoclonal antibody to $H^3$-digoxin was inhibited by cold digoxin and related cardiac glycosides. Fine specificity could be demonstrated by inhibition of binding of monoclonal antibody to $H^3$-digoxin by cold digoxin and other related cardiac glycosides, i.e., digoxin, digitoxigenin, deslanoside, acetyl strophanthidin, and ouabain (FIG. 1).

Figure 1B:
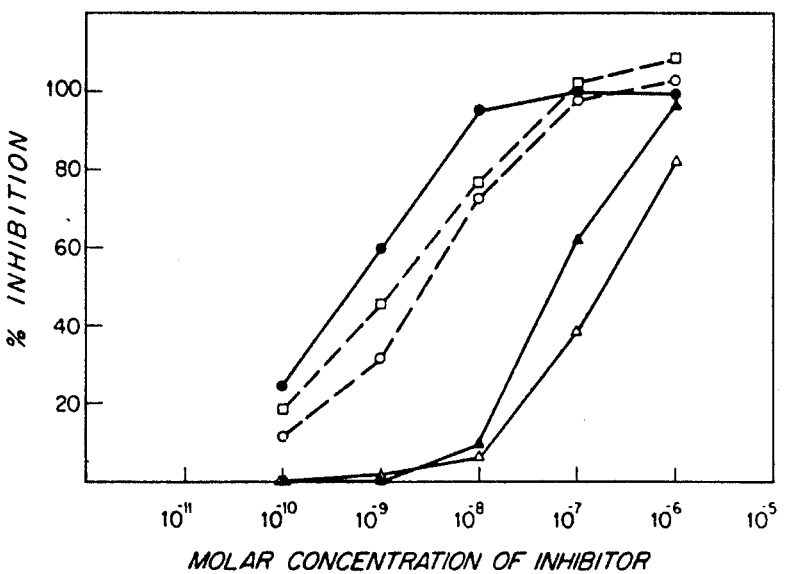
Figure 1C:
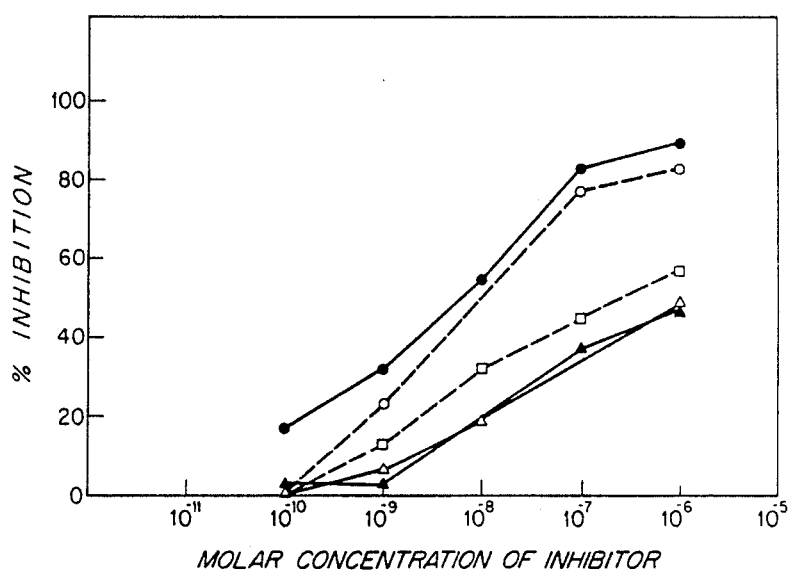

Three of the six anti-digoxin antibodies (Dig 25-54, 26-10, and 35-20), when analyzed for specificity, revealed unique sets of inhibition curves different from each other. The inhibition profile obtained for Dig 26-10 as compared to that for Dig 35-20 and Dig 25-54 is shown in Table IV. For antibody 26-10, all of the cardiac glycosides compete effectively with $H^3$-digoxin for the binding site except ouabain (FIG. 1A). An inhibition profile similar to Dig 26-10 was obtained for Dig 35-20 except that this antibody also had a reduced affinity for acetyl strophanthidin (FIG. 1B).

In contrast to Dig 26-10 and Dig 35-20, the inhibition curves found for Dig 25-54 (FIG. 1C) are all shifted at least an order of magnitude towards higher cardiac glycoside concentrations because of the lower apparent affinity ($K_o < 10^8 M^{-1}$) of this antibody. More importantly, as for Dig 35-20, neither acetyl strophanthidin nor ouabain competes well with $H^3$-digoxin for the Dig 25-54 combining site. It is likely that antibodies 26-10, 35-20, and 25-54 are specific for different portions of the cardiac glycoside ring structures. When compared to Dig 26-10, antibodies 26-20, 26-30 and 26-40 showed nearly identical inhibition curves. No significant inhibition of binding of $H^3$-digoxin by endogenous steroids (cholesterol, testosterone, 17-[beta]-estradiol, progesterone, cortisol, and 4-androstedione) was found for any of the six hybrodomas tested. A summary of the specificity profiles for all six hybridomas is presented in Table IV. The results clearly demonstrate that the behavior or a monoclonal antibody or of a fragment thereof cannot be known in advance and must be tested with particularity and a selection made therefrom.

TABLE IV

Specificity of Hybridoma Antibodies for Various Cardiac Glycosides Relative to Digoxin[a]

| Hybridoma clone or Antisera | Cardiac Glycoside Inhibitors | | | | | |
|---|---|---|---|---|---|---|
| | Digoxin | Digitoxin | Digitoxigenin | Deslanoside | Acetylstrophanthidin | Ouabain |
| Dig 25-54 | 1.0 | 1.8 | 54.0 | 4.3 | >100 | >100 |
| Dig 35-20 | 1.0 | 4.6 | 2.7 | 3.7 | 110 | 333 |

TABLE IV-continued

Specificity of Hybridoma Antibodies for Various Cardiac Glycosides Relative to Digoxin[a]

| Hybridoma clone or Antisera | Cardiac Glycoside Inhibitors | | | | | |
|---|---|---|---|---|---|---|
| | Digoxin | Digitoxin | Digitoxigenin | Deslanoside | Acetylstrophanthidin | Ouabain |
| Dig 26-10 | 1.0 | 1.3 | 3.7 | 2.6 | 1.50 | 66 |
| Dig 26-20 | 1.0 | 1.0 | 2.2 | 1.5 | 0.70 | 53 |
| Dig 26-30 | 1.0 | 2.6 | 3.6 | 1.6 | 0.85 | 84 |
| Dig 26-40 | 1.0 | 1.4 | 4.0 | 2.0 | 2.30 | 78 |
| Sheep Anti-Dig Serum | 1.0 | 152.0 | 860.0 | N.D. | N.D. | >$10^5$ |

[a]Inhibition of binding of antibody to [$^3$H]digoxin by a series of cardiac glycosides was determined for each hybridoma antibody and for a standard sheep antidigoxin serum. The assay system used is the same as that described in Table II. The values reported here are amounts of inhibitor required to give 50% inhibition relative to the amount of digoxin which gave 50% inhibition. Steroids, such as cholesterol, testosterone, 15-β-estradiol, progesterone, cortisol, and 4-androsterone were similarly tested for their ability to inhibit the binding of each hydridoma antibody to [$^3$H]digoxin. None gave any inhibition at the highest concentrations tested ($10^{-4}$ M).

The values listed in Table VI are the molar amounts of cardiac glycoside required to give 50% inhibition relative to the amount of digoxin which gave 50% inhibition in the same system. For example, for the antibody Dig 35-20, 110 times more acetyl strophanthidin than digoxin was required to achieve 50% inhibition. In contrast, for all the Dig 26 hybridomas, acetyl strophanthidin was nearly identical to digoxin in a competition experiment. None of these hybridomas appears to distinguish between digoxin and digitoxin, which differ by only a single hydroxyl group at position 12 on the steroid backbone structure. A heterogeneous sheep antiserum raised to digoxin, however, appears to demonstrate an affinity for these two glycosides which differs by a factor of 150 (Table IV).

Antidigoxin Hybridomas Tested In Clinical Digoxin Radioimmunoassay

Both hybridomas Dig 26-10 and Dig 35-20 demonstrated sufficiently high affinity to be useful in a clinical radioimmunoassay of serum digoxin levels. The results of a RIA utilizing a commercially available kit (Corning, New York) on the sera of 12 patients at the Massachusetts General Hospital are compared to the results of an RIA which employed either sheep antidigoxin sera or hybridomas Dig 26-10 and Dig 35-20 as antidigoxin antibody (Table V).

TABLE V

Monoclonal Antibodies Tested in a Clinical Assay for Digoxin[a]

| | $^{125}$I-RIA Kit[b] | [$^3$H]Digoxin-RIA | | |
|---|---|---|---|---|
| RIA Used: Antidigoxin Ab: | Supplied by Corning | Sheep Antisera Digoxin/ml sera | Dig 26-10 | Dig 35-20 |
| Patient Number | ng/ml | ng/ml | ng/ml | ng/ml |
| 4601 | 2.6 | 2.8 | 2.6 | n.d. |
| 4605 | 0.9 | 1.2 | 0.8 | n.d. |
| 4615 | 0.4 | 0.8 | 0.8 | n.d. |
| 4617 | 0.8 | 1.0 | 0.7 | n.d. |
| 5875 | 1.3 | 1.4 | 1.6 | n.d. |
| 5876 | 1.3 | 1.1 | 1.2 | n.d. |
| 5884 | 1.2 | 1.6 | 1.6 | n.d. |
| 9708 | 4.4 | 4.8 | 5.4 | 6.0 |
| 9717 | 2.5 | 2.3 | 2.1 | 1.9 |
| 9761 | 2.0 | 1.5 | n.d. | 1.6 |
| 2020 | 3.6 | 3.4 | 3.8 | 3.5 |
| 2045 | 0.4 | 0.6 | 0.3 | 0.8 |

[a]Monoclonal antibodies Dig 26-10 and Dig 35-20 were compared to the sheep antidigoxin sera and to antidigoxin antibody from a commercially available kit utilized for their ability to quantitate digoxin in patients' sera.
[b]The commercially available $^{125}$I-RIA kit for quantitating digoxin was purchased from Corning (Corning, New York).

The results listed in column 1, Table V, were obtained from analysis which utilized a commercially available assay kit in which digoxin is tagged with $I^{125}$. The other three assays were performed with the dextran coated charcoal RIA described hereinabove. As seen in Table V, both hybridomas detected comparable levels of digoxin in hyuman serum samples to that detected using a heterogeneous elicited sheep antiserum and a commercial RIA kit.

Gel Isoelectric Focusing of Anti-Digoxin Monoclonal Antibody

Figure 2:
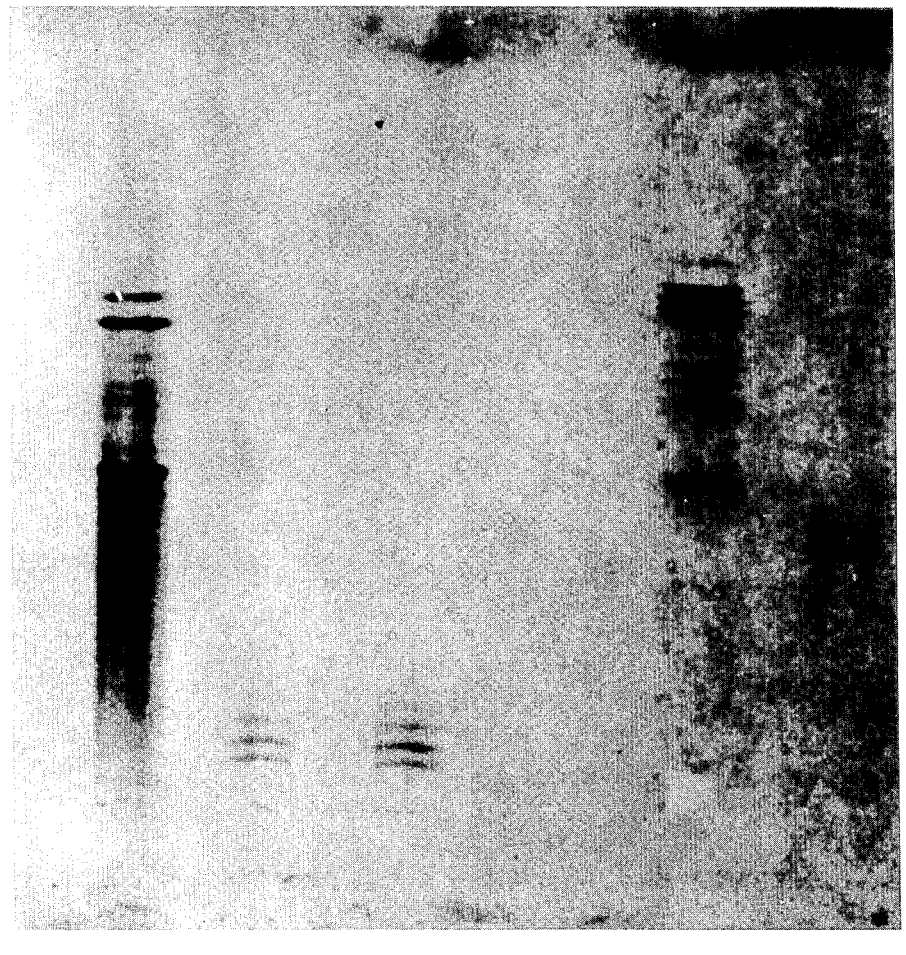
FIG. 2 Gel isoelectric focusing of anti-digoxin antibodies: 1) affinity-purified pooled mouse serum antidigoxin antibodies; 2) monoclonal antibody Dig 26-10 (product of Sp2/0 fusion); 3) Dig 26-20 (product of Sp2/0 fusion) 4) Dig 24-2F8 (product of 45.6TG17 fushion) and 5) Dig 25-54 (product of NSl fusion). Not shown are Dig 26-30 and Dig 26-40, both of which gave banding patterns identical to those of Dig 26-10 and Dig 26-20.

Affinity purified anti-digoxin monoclonal antibodies were compared to one another by gel isoelectric focusing and to heterogeneous anti-digoxin antibody purified from pooled mouse (A/J) immune sera by affinity chromatography. The resulting banding patterns (FIG. 2) clearly demonstrate differences in pI (isoelectric point) for antibodies Dig 26-10, Dig 25-54, and Dig 24-2F8. It should be noted that Dig 35-20 has a pI different from the other antibodies. None of the banding patterns exactly correlates with the major bands seen in the pool of mouse anti-digoxin antibodies. The banding patterns of Dig 26-10 are identical to those of Dig 26-20 and the banding patterns obtained for Dig 26-30 and Dig 26-40 were also identical to Dig 26-10. Thus, these four monoclonal antibodies obtained from fusion 26 possess identical pIs and are, therefore, equally well suited for use in clinical, therapeutic or diagnostic purposes including the reversal of the toxic effects of either digoxin or digitoxin.

Antibody 26-10 was tested further for its ability to reverse established digoxin toxicity in an animal model. In preliminary experiments, digoxin toxicity was experimentally induced in three 2-3 kg cats by the intravenous administration of 0.15-0.20 mg of digoxin per kilogram. Toxicity was manifested by sustained ventricular tachycardia. This toxic effect of digoxin was rapidly reversed in 2 out of 3 animals by a one-fold stoichiometric excess of anti-digoxin hybridoma 26-10. The hybridoma was purified from ascites fluid by DEAE cellulose chromatography for this experiment. Equivalent amounts of normal mouse IgG did not reverse toxicity in control animals.

The demonstration of the reversal of the pharmacologic, therapeutic, and toxic effects of digoxin using specific antibody may prove to be an important model system. It may be pointed out that advantageous use can also be made of fragments of the monoclonal antibodies, e.g. Fab fragments or Fv. The amount of the monoclonal antibodies necessary to reverse digoxin toxicity would depend on the amount of the digoxin present in the body fluid. An effective amount sufficient to substantially reverse digoxin toxicity may range from 50 mg to 50 g depending on the body weight, toxicity level and the like. Initially a provocative dose of the purified antibodies may be administered to monitor the host response to the antibodies. Then, if indicated, a therapeutic dose of the antibodies may be administered, preferably intravenously, in a suitable carrier or physiologically acceptable medium.

It is understood that the description, examples and embodiments contained herein are for illustrative purposes only and that various modifications or changes in light thereof will be suggested to persons skilled in the art and are to be included within the spirit and purview of this application and the scope of the appended claims.

What is claimed as new and desired to be secured by letters patent of the United States is:

1. A hybridoma capable of secreting antidigoxin antibodies which is ATCC HB-8113.
2. An antibody material comprising monoclonal antidigoxin antibodies or fragments thereof produced by hybridoma ATCC HB-8113.

* * * * *